(12) United States Patent
Yamawaki et al.

(10) Patent No.: US 11,467,073 B2
(45) Date of Patent: Oct. 11, 2022

(54) METHOD FOR CONCENTRATING EXTRACELLULAR VESICLES

(71) Applicant: SYSMEX CORPORATION, Kobe (JP)

(72) Inventors: Koya Yamawaki, Kobe (JP); Yuki Aihara, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 166 days.

(21) Appl. No.: 15/935,445

(22) Filed: Mar. 26, 2018

(65) Prior Publication Data

US 2018/0275029 A1  Sep. 27, 2018

(30) Foreign Application Priority Data

Mar. 27, 2017  (JP) .............................. JP2017-060480

(51) Int. Cl.
*G01N 1/40* (2006.01)
*B01D 17/02* (2006.01)

(52) U.S. Cl.
CPC ....... *G01N 1/4055* (2013.01); *B01D 17/0217* (2013.01); *G01N 1/4077* (2013.01); *C12Q 2563/161* (2013.01)

(58) Field of Classification Search
CPC . G01N 1/4055; G01N 1/4077; B01D 17/0217
See application file for complete search history.

(56) References Cited

U.S. PATENT DOCUMENTS

| 8,901,284 B2 | 12/2014 | Vlassov et al. | |
| 10,590,372 B2* | 3/2020 | Park | C12Q 1/24 |
| 11,016,009 B2* | 5/2021 | Park | G01N 33/5306 |
| 2007/0048786 A1* | 3/2007 | Chait | C07K 1/36 435/7.1 |
| 2013/0273544 A1 | 10/2013 | Vlassov et al. | |
| 2014/0178888 A1* | 6/2014 | Vlassov | G01N 33/5076 435/6.12 |

(Continued)

FOREIGN PATENT DOCUMENTS

| CN | 106399250 A | 2/2017 | |
| JP | 2017-038566 A | 2/2017 | |
| WO | WO-2016159520 A1 * | 10/2016 | .............. C12M 1/26 |

OTHER PUBLICATIONS

Moody, M.L. et al. "Solvent Property Characterization of Poly(ethylene glycol)/Dextran Aqueous Biphasic Systems Using the Free Energy of Transfer of a Methylene Group and a Linear Solvation Energy Relationship," Ind. Eng. Chem. Res. 2005, 44, 10, 3749-3760 (Year: 2005).*

(Continued)

*Primary Examiner* — Jennifer Wecker
*Assistant Examiner* — Michelle Adams
(74) *Attorney, Agent, or Firm* — Sughrue Mion, PLLC (57) ABSTRACT

Disclosed is a method for concentrating extracellular vesicles, comprising preparing a mixture comprising a first fraction and a second fraction by mixing a liquid sample comprising extracellular vesicles, a polysaccharide, and a polyether having an average molecular weight of 20,000 or less, wherein the first fraction comprises a higher concentration of extracellular vesicles than the second fraction, and the first fraction comprises a higher concentration of extracellular vesicles than the liquid sample.

10 Claims, 5 Drawing Sheets

(56) References Cited

U.S. PATENT DOCUMENTS

2016/0216253 A1    7/2016  Balaj et al.
2018/0164197 A1*  6/2018  Park .................... G01N 1/40
2019/0231692 A1*  8/2019  Katakowski .......... A61K 35/19

OTHER PUBLICATIONS

Sousa, A.F. et al. "A novel method for human hematopoietic stem/progenitor cell isolation from umbilical cord blood based on immunoaffinity aqueous two-phase partitioning," Biotechnol Lett (2011) 33:2373-2377 (Year: 2011).*
Robbins, K.M. et al. "The Isolation and Characterization of Right-Side-Out Plasma Membrane Vesicles from Barley Aleurone Cells," Paper No. L7941 in Lipids 34, 75-82 (1999). (Year: 1999).*
Atefi, E. et al. "Characterization of Aqueous Two-Phase Systems from Volume and Density Measurements," J. Chem. Eng. Data 2016, 61, 1531-1539 (Year: 2016).*
Shanbhag, V.P., et al. "A new method for the determination of the binding capacity of testosterone-estradiol-binding-globulin in human plasma," Journal of Steroid Biochemistry vol. 4, Issue 5, Sep. 1973, pp. 537-550 (Year: 1973).*
Agilent Technologies. "Polymer Molecular Weight Distribution and Definitions of MW Averages." Printed in the USA, Apr. 30, 2015. 5990-7890EN. (Year: 2015).*
Albertsson, P.-A. "Partition of Cell Particles and Macromolecules in Polymer Two-Phase Systems," Advances in Protein Chemistry. vol. 24, 1970, pp. 309-341 (Year: 1970).*
Park, Y.H. et al. "Prostate-specific extracellular vesicles as a novel biomarker in human prostate cancer," Sci. Rep. 6, 30386; doi: 10.1038/srep30386 (2016). Published: Aug. 9, 2016 (Year: 2016).*
King, R.S. et al. "Molecular thermodynamics of aqueous two-phase systems for bioseparations," AIChE Journal vol. 34, Issue10 , Oct. 1988, 1585-1594 (Year: 1988).*
Hyunwoo Shin et al., "High-yield isolation of extracellular vesicles using aqueous two-phase system", Scientific Reports, 2015, 5, Article No. 13103, pp. 1-11.
Jongmin Kim et al., "Isolation of High-Purity Extracellular Vesicles by Extracting Proteins Using Aqueous Two Phase System", PLoS ONE, DOI: 10.1371/journal.pone.0129760, Jun. 19, 2015, pp. 1-16.
Japanese Office Action dated Feb. 9, 2021 in a counterpart Japanese patent application No. 2017-060480.

* cited by examiner

METHOD FOR CONCENTRATING EXTRACELLULAR VESICLES

CROSS REFERENCE TO RELATED APPLICATIONS

This application claims priority from prior Japanese Patent Application No. 2017-060480, filed on Mar. 27, 2017 entitled "Method for concentrating extracellular vesicles and reagent for concentrating extracellular vesicles", the entire contents of which are incorporated herein by reference.

TECHNICAL FIELD

The present invention relates to a method for concentrating extracellular vesicles.

BACKGROUND

Various extracellular vesicles such as exosomes are known to be released from the inside to the outside of cells. Extracellular vesicles are known to be present in liquid samples such as blood, saliva, and lymph. Recently, the presence of extracellular vesicles and the relationship between molecules, such as miRNAs and proteins, contained in extracellular vesicles and diseases have been actively studied, and the use of extracellular vesicles or molecules contained in extracellular vesicles as a medical biomarker has attracted attention. However, the concentration of extracellular vesicles is generally low. Therefore, extracellular vesicles are preferably concentrated to detect extracellular vesicles or a marker contained in extracellular vesicles. As a method for concentrating extracellular vesicles, a method is disclosed in which two-phase partitioning between polyethylene glycol and dextran is utilized to collect extracellular vesicles from a lower dextran fraction (Balaj, N et al., Scientific Reports, 5, Article number: 13103 (2015), Kim, J et al., PLoS ONE, DOI: 10.1371/journal.pone.0129760 Jun. 19, 2015). Further, polymeric precipitation kits for precipitating and collecting extracellular vesicles are also commercially available.

SUMMARY

The scope of the present invention is defined solely by the appended claims, and is not affected to any degree by the statements within this summary.

The present inventors have intensively studied and found that extracellular vesicles contained in a liquid sample can be concentrated and collected at a high collection rate by two-phase partitioning using a polysaccharide and a polyether having a relatively low molecular weight. This finding has led to the completion of the present invention.

A first aspect of the present invention is directed to a method for concentrating extracellular vesicles. The method comprises preparing a mixture comprising a first fraction and a second fraction by mixing a liquid sample comprising extracellular vesicles, a polysaccharide, and a polyether having an average molecular weight of 20,000 or less. The first fraction comprises a higher concentration of extracellular vesicles than the second fraction, and the first fraction comprises a higher concentration of extracellular vesicles than the liquid sample.

A second aspect of the present invention is directed to a method for concentrating extracellular vesicles. The method comprises preparing a mixture comprising a first fraction and a second fraction by (i) mixing a liquid sample comprising extracellular vesicles, a polysaccharide, and a polyether having an average molecular weight of 20,000 or less, (ii) stirring the mixture, and (iii) centrifuging the mixture, wherein the first fraction comprises a higher concentration of extracellular vesicles than the second fraction, and the first fraction comprises a higher concentration of extracellular vesicles than the liquid sample; collecting the first fraction.

A third aspect of the present invention is directed to a method for concentrating extracellular vesicles, comprising: preparing a mixture comprising a first fraction and a second fraction by (i) mixing a liquid sample comprising extracellular vesicles, a polysaccharide, and a polyether having an average molecular weight of 20,000 or less, (ii) stirring the mixture, and (iii) centrifuging the mixture, wherein the first fraction comprises a higher concentration of extracellular vesicles than the second fraction, and the first fraction comprises a higher concentration of extracellular vesicles than the liquid sample; collecting the first fraction; and dispersing extracellular vesicles in the first fraction.

DETAILED DESCRIPTION OF THE PREFERRED EMBODIMENTS

Explanation of Terms

Terms used in this specification will be first explained. Unless otherwise specified, terms used in the present invention shall be interpreted on the basis of the description in this section.

Extracellular vesicles are particles that are released from cells, have a size of about several tens to several thousands of nanometers, and are coated with a membrane mainly containing phospholipid. The extracellular vesicles include exosomes, microvesicles, apoptotic bodies, etc. In many cases, biomolecules are present in the extracellular vesicles. For example, exosomes or microvesicles contain at least one kind of biomolecules selected from the group consisting of polypeptides and nucleic acids (RNAs such as mRNAs, miRNAs, and non-coding RNAs).

For example, apoptotic bodies contain at least one selected from the group consisting of fragmented nucleus and organelles. The extracellular vesicles preferably contain at least one kind of biomolecules selected from the group consisting of polypeptides and RNAs.

The extracellular vesicles may contain at least one kind of biomolecules selected from the group consisting of polypeptides and RNAs. Here, the polypeptides refer to compounds in which a plurality of amino acids are linked via peptide bonds. The "polypeptide" comprises a protein and a peptide. A protein has a relatively high molecular weight and peptide has a relatively low molecular weight.

A liquid sample is a sample of a liquid component taken from an animal or a plant. Specific examples of the liquid sample taken from an animal include blood serum, blood plasma, lymph, urine, ascites, pleural effusion, cerebrospinal fluid, and interstitial fluid. Specific examples of the liquid sample taken from a plant include interstitial fluid, xylem sap, and phloem sap.

A polysaccharide contains at least one selected from the group consisting of a homopolysaccharide, a heteropolysaccharide, and salts thereof. The homopolysaccharide refers to a polysaccharide having a sugar skeleton constituted from one kind of monosaccharide. Preferred examples of the homopolysaccharide include polysaccharides composed of one kind of monosaccharide selected from the group consisting of glucose, fructose, galactose, and glucosamine. The homopolysaccharide is more preferably a polysaccharide composed of glucose.

A heteropolysaccharide refers to a polysaccharide having a sugar skeleton constituted from at least two kinds of monosaccharides. Preferred examples of the heteropolysaccharide include polysaccharides composed of two or more kinds of monosaccharides selected from the group consisting of glucose, fructose, galactose, glucosamine, mannose, and idose. The heteropolysaccharide is more preferably a polysaccharide composed of two or more kinds of monosaccharides selected from the group consisting of glucose, glucosamine, and idose.

The sugar skeleton refers to a basic skeleton from which a substituent possessed by a monosaccharide is removed. For example, N-acetylglucosamine has glucosamine as a sugar skeleton and an acetyl group as a substituent. Glucuronic acid has glucose as a sugar skeleton and a carboxyl group as a substituent. Iduronic acid has idose as a sugar skeleton and a carboxyl group as a substituent. Mannuronic acid has mannose as a sugar skeleton and a carboxyl group as a substituent.

More specifically, the polysaccharide preferably contains at least one selected from the group consisting of dextran, heparin, chitin, inulin, alginic acid, cellulose, methyl cellulose, and salts thereof. The polysaccharide is preferably dextran.

Examples of the salts of the polysaccharide include sodium salts, potassium salts, and calcium salts of the polysaccharide.

The polysaccharide has an average molecular weight of 3,000 to 800,000 as a weight-average molecular weight. The lower limit of average molecular weight of the polysaccharide is preferably 10,000, more preferably 100,000, even more preferably 400,000. The upper limit of average molecular weight of the polysaccharide is preferably 700,000. The average molecular weight of the polysaccharide is most preferably 450,000 to 650,000.

The weight-average molecular weight of the polysaccharide can be determined by gel permeation chromatography (GPC) analysis by comparison with molecular weight standards having known molecular weight distributions of a polysaccharide that is the same kind as the polysaccharide to be measured.

A polyether refers to a polymer having a plurality of ether bonds. The polyether is preferably a polymer in which alkylene glycol units are linked via ether bonds. The alkylene is a linear alkylene having 1 to 6 carbon atoms or a branched alkylene having 3 to 6 carbon atoms. The alkylene is preferably a linear alkylene having 1 to 3 carbon atoms or a branched alkylene having 3 carbon atoms. The polyether more preferably contains at least one selected from the group consisting of polyethylene glycol, polypropylene glycol, polytetramethylene glycol, and a mixture of two or more of them. The polyether is even more preferably at least one selected from the group consisting of polyethylene glycol, polypropylene glycol, and a mixture of them, and is even more preferably polyethylene glycol.

The average molecular weight of the polyether as determined by the following titration method is 20,000 or less, preferably 10,000 or less, more preferably 6,000 or less. The average molecular weight of the polyether is preferably 2,000 or more. When a preferred range of average molecular weight of the polyether is represented as a standard value that represents the range of average molecular weight distribution of the polyether, the lower limit of the range of 1,500, preferably 2,700, more preferably 7,400. The upper limit of the range is 25,000, preferably 10,200. The most preferred range of average molecular weight of the polyether represented as a standard value is 7,400 to 10,200.

The average molecular weight of the polyether can be determined by the following titration method.

(a) First, 20.0000 g of a polyether whose average molecular weight is to be measured is precisely weighed and placed in a 100 mL-pressure bottle.

(b) Then, 25 mL of a phthalic anhydride-pyridine solution precisely weighed is added to the pressure bottle containing the polyether, and the pressure bottle is hermetically sealed. Here, the phthalic anhydride-pyridine solution is prepared by placing 42 g of phthalic anhydride precisely weighed in a light-blocking bottle with stopper, adding 300 mL of pyridine precisely weighed thereto, and allowing the mixture to stand for 16 hours or more to dissolve phthalic anhydride.

(c) The pressure bottle containing the solution is placed in a liquid previously heated to 96 to 100° C. and contained in a water bath, and is allowed to stand for 2 hours.

(d) The pressure bottle is taken out of the water bath and cooled at room temperature.

(e) After cooling, the solution contained in the pressure bottle is transferred to a 300 mL conical flask while the pressure bottle is washed with pyridine.

(f) Then, 50 mL of a 0.5 mol/L sodium hydroxide solution precisely weighed is added to the conical flask used in (e), and 10 drops of a 10 g/L phenolphthalein-pyridine solution are further added dropwise.

(g) The solution in the conical flask obtained in (f) is titrated with a 0.5 mol/L sodium hydroxide solution to determine a titer a (mL). The end point of the titration is a point such that the solution is kept red for 15 seconds.

(h) The above steps (b) to (g) are performed separately as a blank test without adding the polyether to determine a titer b (mL).

(i) The average molecular weight of the polyether is determined from the following calculation formulas 1 and 2.

$$A = \frac{28.05 \times (b-a) \times f}{S} \quad \text{[Calculation Formula 1]}$$

$$B = \frac{56108 \times 2}{A} \quad \text{[Calculation Formula 2]}$$

In the above calculation formulas, A represents the hydroxyl value of the polyether, B represents the average molecular weight of the polyether, S represents the mass (g) of the sample measured off, and f represents the titer (factor) of the 0.5 mol/L sodium hydroxide solution.

Mixing is intended to mix materials required in each of the steps of a method that will be described later. A mixture may be in a state where all or some of components contained therein are dispersed or dissolved, or may contain two or more separated liquid phases.

A first fraction is a polysaccharide fraction containing at least the polysaccharide. Preferably, the first fraction is substantially free from the polyether. A second fraction is a polyether fraction containing at least the polyether. Preferably, the second fraction is substantially free from the polysaccharide. Here, the phrase "substantially free from the polyether" means that the first fraction may contain a trace amount of the polyether as long as advantageous effects disclosed herein are not impaired. The phrase "substantially free from the polysaccharide" means that the second fraction may contain a trace amount of the polysaccharide as long as advantageous effects disclosed herein are not impaired. The first fraction contains a higher concentration of extracellular vesicles than the second fraction. The second fraction contains a lower concentration of extracellular vesicles than the first fraction or contains substantially no extracellular vesicles.

A state in which the first fraction and the second fraction are separated refers to a state where the first fraction and the second fraction undergo phase separation. The boundary between the first and second phases does not need to be clearly visible as long as at least two fractions different in the concentration of extracellular vesicles can be obtained. Two fractions separated by a clearer boundary may be obtained by centrifugation or the like.

A unit w/v % represents mass/volume %.

The present disclosure includes several aspects.

[Method for Concentrating Extracellular Vesicles]

A first aspect relates to a method for concentrating extracellular vesicles in vitro.

More specifically, the method according to the first aspect comprises the step of preparing a mixture of a liquid sample containing extracellular vesicles, a polysaccharide, and a polyether having an average molecular weight of 20,000 or less. The mixture contains at least a first fraction and a second fraction. In the first fraction, extracellular vesicles are present in a dispersed, sedimented, or pelletized state. The first fraction contains a higher concentration of extracellular vesicles than the second fraction. The first fraction contains a higher concentration of extracellular vesicles than the liquid sample.

Here, the phrase "concentrating extracellular vesicles" means that a liquid containing a higher concentration of extracellular vesicles than a liquid sample is prepared. The concentrating method according to this aspect can be used as a preprocessing method (pretreatment method) for detecting extracellular vesicles or a marker contained in extracellular vesicles.

The content of the polysaccharide in the mixture is 2 w/v % or more, preferably 5 w/v % or more as a final concentration. The upper limit of the polysaccharide content is 8 w/v %.

The content of the polyether in the mixture is 4 w/v % or more, preferably 5 w/v % or more as a final concentration. The upper limit of the polyether content is 10 w/v %, preferably 8 w/v %.

The final concentration ratio between the polysaccharide and the polyether in the mixture is 8:2 to 4:8, preferably 8:2 to 5:5. When the molecular weight of the polyether is 2,700 to 3,500 as a standard value of average molecular weight, the final concentration ratio between the polysaccharide and the polyether in the mixture is preferably 10:5 to 4:8. When the molecular weight of the polyether is 15,000 to 25,000 as a standard value of average molecular weight, the final concentration ratio between the polysaccharide and the polyether in the mixture is preferably 8:2 to 5:5. The final concentration ratio is based on mass.

The polysaccharide and the polyether to be mixed with the liquid sample may be either solid or liquid. The polysaccharide or the polyether may be dissolved in a solvent before mixed with the solid sample. Examples of the solvent include water, normal saline, and a buffer solution (e.g., PBS).

The method according to this aspect may further comprise the step of collecting the first fraction after the step of preparing a mixture. A method for collecting the first fraction is not particularly limited as long as the whole or part of the first fraction can be obtained separately from the second fraction. For example, the collecting method includes removing the second fraction to leave the first fraction after phase separation between the first fraction and the second fraction or aspirating the first fraction into a pipette and, if necessary, transferring the first fraction to another container.

The method according to this aspect may comprise, after the step of preparing a mixture but before the step of collecting the first fraction, the step of centrifuging the mixture to cause clearer phase separation between at least the first fraction and the second fraction. According to this aspect, it is possible to easily cause phase separation even at a lower centrifugal acceleration than ever before. For example, the centrifugal acceleration may be less than 10,000 g, 5,000 g or less, or 3,000 g or less. The lower limit of the centrifugal acceleration is preferably 1,000 g. The centrifugal acceleration is preferably in the range of 1,000 to 3,000 g. The time of centrifugation is preferably 2 minutes or less, more preferably 1 minute 30 seconds or less, even more preferably 1 minute or less. The lower limit of the time of centrifugation is preferably 30 seconds. The temperature of centrifugation is not particularly limited as long as it is the temperature of a working atmosphere. The temperature of centrifugation is preferably 5° C. to 40° C.

The method according to this aspect may comprise, after the step of preparing a mixture but before the step of centrifuging the mixture, the step of stirring the mixture. A method for stirring the mixture is not particularly limited, and the mixture may be stirred with a vortex mixer or by pipetting 2 to 5 times.

[Method for Detecting Extracellular Vesicles and Method for Detecting Biomolecules]

A second aspect relates to a method for detecting extracellular vesicles in vitro.

More specifically, the method according to the second aspect comprises the step of preparing a mixture of a liquid sample containing extracellular vesicles, a polysaccharide, and a polyether having an average molecular weight of 20,000 or less. The mixture contains at least a first fraction and a second fraction. In the first fraction, extracellular vesicles are present in a dispersed, sedimented, or pelletized state. The first fraction contains a higher concentration of extracellular vesicles than the second fraction. The first fraction contains a higher concentration of extracellular vesicles than the liquid sample.

The method for detecting extracellular vesicles comprises the step of collecting the first fraction and the step of detecting extracellular vesicles in the first fraction.

Extracellular vesicles can be detected according to a known method for detecting particles. For example, extracellular vesicles can be detected using an optical microscope, an electron microscope, a flow cytometer, or the like. Here, the term "detecting" includes qualitatively detecting, quantitating, and semi-quantitatively detecting. Here, the term "semi-quantitatively detecting" means that a concentration is categorized in levels such as "negative", "slightly positive", and "most positive."

Biomolecules present in extracellular vesicles can be detected according to a known method for detecting biomolecules. For example, when the biomolecules are proteins or polypeptides, they can be detected by ELISA method or Western blotting method. For example, when the biomolecules are nucleic acids, they can be detected by PCR method, RT-PCR method, or microarray method.

In other words, a method for detecting biomolecules according to a third aspect can be implemented by replacing the step of detecting extracellular vesicles in the first fraction of the method according to the second aspect with the step of detecting biomolecules contained in extracellular vesicles in the first fraction.

The method according to the second aspect and the method according to the third aspect may comprise, after the step of preparing a mixture but before the step of collecting the first fraction, the step of centrifuging the mixture to cause clearer phase separation between at least the first fraction and the second fraction.

The method according to the second aspect and the method according to the third aspect may comprise, after the step of preparing a mixture but before the step of centrifuging the mixture, the step of stirring the mixture.

In the method according to the second aspect and the method according to the third aspect, when extracellular vesicles are present in the solution in a sedimented or pelletized state after the step of collecting the first fraction, the step of dispersing extracellular vesicles may be performed before the detecting step (i.e., before the step of detecting extracellular vesicles or the step of detecting biomolecules). In such a dispersing step, extracellular vesicles may be dispersed in the first fraction or in another solvent such as water, normal saline, or a buffer solution (e.g., PBS).

For the steps and the operations common to the first, second, and third aspects, the description thereof made with reference to the first aspect is incorporated herein. For the terms common to the first, second, and third aspects, the description thereof made with reference to the first aspect is incorporated herein.

[Reagent for Concentrating Extracellular Vesicles and Kit for Concentrating Extracellular Vesicles]

A fourth aspect relates to a reagent for concentrating extracellular vesicles, comprising at least one selected from the group consisting of a polysaccharide and a polyether having an average molecular weight of 20,000 or less.

In the reagent according to the fourth aspect, the polysaccharide or the polyether having an average molecular weight of 20,000 or less may be in the form of either a solid or a solution.

A fifth aspect relates to a kit for concentrating extracellular vesicles, comprising a polysaccharide and a polyether having an average molecular weight of 20,000 or less. The kit disclosed herein includes one constituted from one container.

In the fifth aspect, the phrase "comprising a polysaccharide and a polyether having an average molecular weight of 20,000 or less" is used to mean that (i) the kit includes a mixed reagent containing both a polysaccharide and a polyether from the beginning, that is, the kit includes one container containing a polysaccharide and a polyether, (ii) a polysaccharide and a polyether are packaged separately from each other and provided in combination, or (iii) a polysaccharide and a polyether are packaged separately from each other, distributed to the market through different marketing channels, and used in combination.

Figure 6:
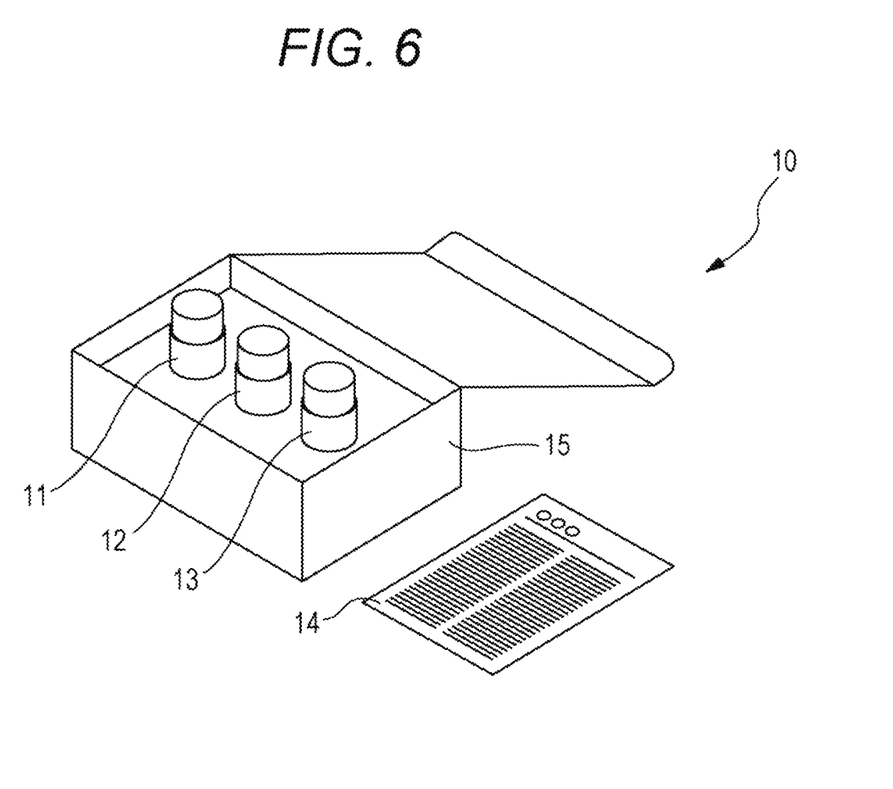
FIG. 6 is a schematic diagram showing an example of a kit for concentrating extracellular vesicles.

An example of the kit is shown in FIG. 6. A kit 10 includes a first container 11 containing a polysaccharide and a second container 12 containing a polyether having an average molecular weight of 20,000 or less. The kit 10 may further include a third container 13 containing a solvent such as water, normal saline, or a buffer solution (e.g., PBS). The kit 10 may further include a box 15. The kit 10 may further include paper 14 containing its instruction manual or the URL of a website where users can access its instruction manual.

In the kit according to the fifth aspect, the polyether having an average molecular weight of 20,000 or less or the polysaccharide may be in the form of either a solid or a solution.

Examples of a solvent to be used for preparing the solution in the fourth and fifth aspects include water, normal saline, and a buffer solution (e.g., PBS). The concentration of the polysaccharide or the polyether in the solution is not limited as long as the final concentration of the polysaccharide or the polyether in the mixture described above with reference to the method for concentrating extracellular vesicles can be achieved.

In this specification, the phrase "comprising a polysaccharide and a polyether having an average molecular weight of 20,000 or less" includes all the meanings of the phrases "containing a polysaccharide and a polyether having an average molecular weight of 20,000 or less", "essentially consisting of a polysaccharide and a polyether having an average molecular weight of 20,000 or less", and "consisting of a polysaccharide and a polyether having an average molecular weight of 20,000 or less".

The present disclosure includes the use of a polysaccharide and a polyether having an average molecular weight of 20,000 or less for producing a reagent for concentrating extracellular vesicles or a kit for concentrating extracellular vesicles. The reagent for concentrating extracellular vesicles and the kit for concentrating extracellular vesicles are as described above.

EXAMPLES

The present invention will be specifically described with reference to the following examples, but the present invention should not be construed as limited to these examples.

Experimental Example 1: Examination of Liquid-Liquid Phase Separation

1. Method

In order to examine the influence of the molecular weight of a polyether on phase separation and the influence of the ratio between a polyether and a polysaccharide on phase separation, an experiment was performed according to the following protocol. Polyethylene glycol (hereinafter abbreviated as "PEG") was used as a polyether, and dextran (hereinafter abbreviated as "Dex") was used as a polysaccharide.

(1) A 30 w/v % aqueous PEG (NACALAI TESQUE, INC.) solution and a 30 w/v % aqueous Dex (Sigma-Aldrich (USA), average molecular weight: 450,000 to 650,000) solution were added to 200 μL of a sample (water, PBS, or a culture medium) so that a final total volume was 300 μL. That is, the total volume of the aqueous PEG solution and the aqueous Dex solution was 100 μL. For the examination of the influence of the average molecular weight of PEG on phase separation, 50 μL of an aqueous solution of PEG having an average molecular weight shown in Table 1 and 50 μL of an aqueous Dex solution were added to a sample. For the examination of the influence of the ratio between PEG and Dex on phase separation, PEG having an average molecular weight of 15,000 to 25,000 was used, and an aqueous PEG solution and an aqueous Dex solution were mixed so that the mixed solution had final concentrations of PEG and Dex shown in Tables 2 and 3. The culture medium used was prepared by adding 10% (final concentration) FBS (HycloneLaboratories, GE Healthcare Japan) and 100-fold diluted Gibco (trademark) Antibiotic-Antimycotic (Thermo Fisher Scientific, 15240-062) to RPMI-1640 medium (Sigma-Aldrich, R8758).

(2) After the aqueous PEG solution and the aqueous Dex solution were added to the sample, the mixture was stirred several times by pipetting.

Figure 1A:
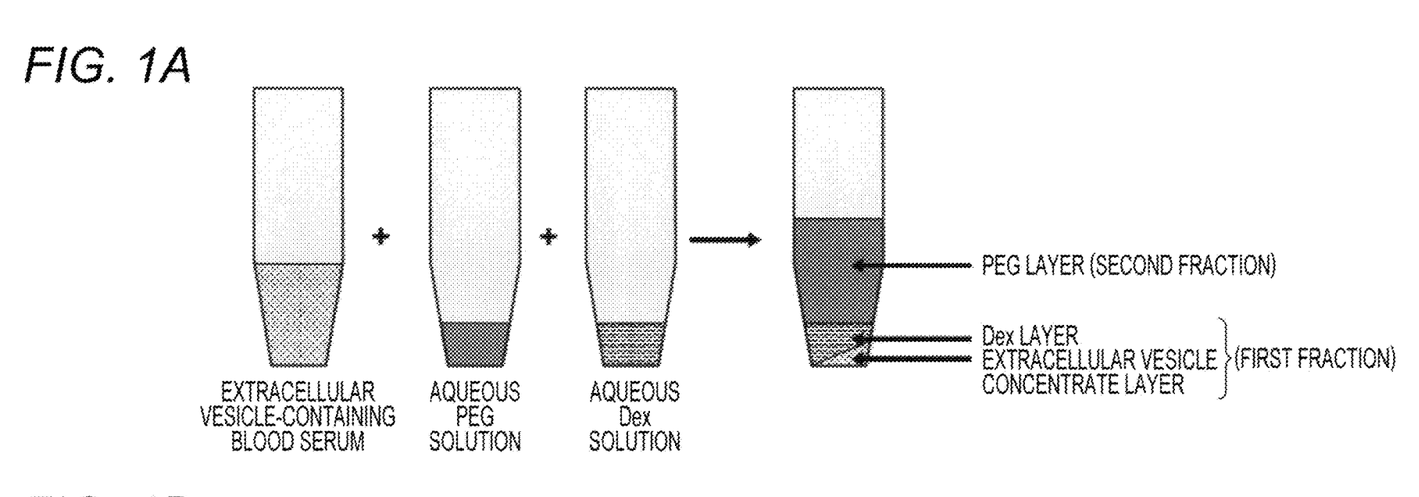
FIG. 1A schematically shows a method for concentrating extracellular vesicles according to the present invention.
Figure 1B:
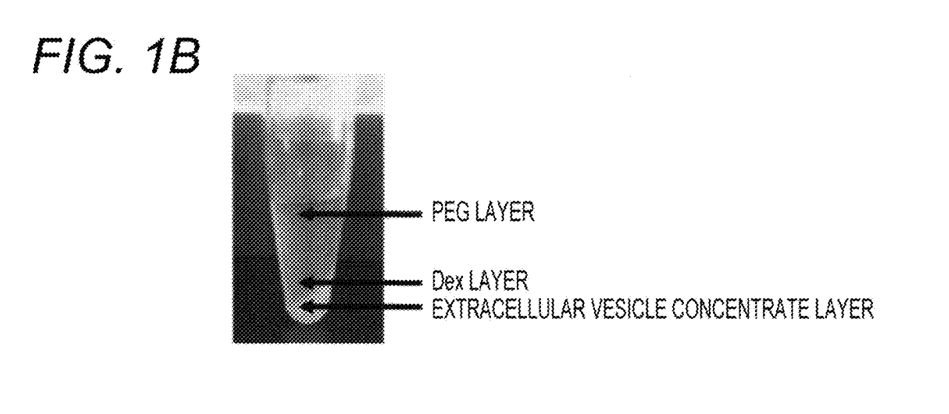
FIG. 1B shows a photograph of a tube after actual centrifugation.

(3) After the pipetting, the mixture was centrifuged using a tabletop centrifugal separator at 1,260 to 2,840 g for 1 minute. FIG. 1A is a schematic diagram showing the above steps. FIG. 1B shows a photograph of a tube after actual centrifugation.

2. Results 2-1. Influence of Molecular Weight of Polyether on Phase Separation

The presence or absence of liquid-liquid phase separation was examined using PBS as a sample and PEGs having different average molecular weights.

As shown in Table 1, liquid-liquid phase separation was observed when PEG having an average molecular weight of 2,700 or more was used.

TABLE 1

| Influence of molecular weight of PEG | |
|---|---|
| Product name of PEG (Standard value of average molecular weight; Test value of average molecular weight) | Presence or absence of phase separation |
| PEG4000 (2,700-3,500; 2,984) | ○ |
| PEG6000 (7,400-10,200; 8,980) | ○ |
| PEG20000 (15,000-25,000; 18,400) | ○ |
| PEG35000 (25,000-45,000; 32,408) | ○ |

*1: In the table, "○" indicates that the liquid phase was separated into two layers.
*2: The standard value of average molecular weight represents a range including the average molecular weight of the polymer.
*3: The test value of average molecular weight is an average molecular weight actually measured by the reagent manufacturer.

2-2. Influence of Ratio Between PEG and Dex on Phase Separation (1) In the Case of PEG20000

The presence or absence of phase separation was examined by changing the ratio between PEG20000 and Dex.

The examination was performed according to the above protocol except that PEG and Dex were mixed so that the final concentrations of PEG and Dex shown in Table 2 were achieved. As shown in Table 2, liquid-liquid phase separation was observed when the final concentration ratio between PEG and Dex was 5:5 to 8:2.

TABLE 2

| Influence of ratio between PEG and Dex (PEG20000) | | |
|---|---|---|
| Final concentration (w/v %) | | Presence or absence of phase separation |
| PEG | Dex | |
| 0 | 10 | X |
| 5 | 5 | ○ |
| 6 | 4 | ○ |
| 7 | 3 | ○ |
| 8 | 2 | ○ |
| 10 | 0 | X |

*1: In the table, "○" indicates that the liquid phase was separated into two layers. In the table, "X" indicates that the liquid phase was not sufficiently separated into two layers.

(2) In the Case of PEG 4000

The presence or absence of phase separation was examined in the same manner as described above using PEG4000 and Dex.

The examination was performed according to the above protocol except that PEG and Dex were mixed so that the final concentrations of PEG and Dex shown in Table 3 were achieved. As shown in Table 3, liquid-liquid phase separation was observed when the final concentration ratio between PEG and Dex was 4:8 to 10:5.

TABLE 3

| Influence of ratio between PEG and Dex (PEG4000) | | |
|---|---|---|
| Final concentration (w/v %) | | Presence or absence of phase separation |
| PEG | Dex | |
| 4 | 8 | ○ |
| 10 | 5 | ○ |

*1: In the table, "○" indicates that the liquid phase was separated into two layers.

From the results of (1) and (2), it was considered that phase separation was likely to occur when the concentration of PEG in the mixed solution was higher.

2-3. Influence of Ratio Between Polyether and Dextran on Volumes of Upper and Lower Layers of Liquid Phase The volume ratio between the two upper and lower layers of the liquid phase separated by centrifugation was determined according to the above protocol using water, PBS, or a culture medium as a sample except that PEG and Dex were mixed so that the final concentrations of PEG and Dex shown in Tables 4 to 6 were achieved.

TABLE 4

Ratio between upper layer and lower
layer after phase separation in water

| Final concentration (w/v %) | | Upper layer (μL) | Lower layer (μL) |
|---|---|---|---|
| PEG | Dex | | |
| 5 | 5 | 200 | 100 |
| 6 | 4 | 220 | 80 |
| 7 | 3 | 240 | 60 |
| 8 | 2 | 260 | 40 |

TABLE 5

Ratio between upper layer and lower layer
after phase separation in PBS

| Final concentration (w/v %) | | Upper layer (μL) | Lower layer (μL) |
|---|---|---|---|
| PEG | Dex | | |
| 5 | 5 | 170 | 130 |
| 6 | 4 | 200 | 100 |
| 7 | 3 | 250 | 50 |
| 8 | 2 | 270 | 30 |

TABLE 6

Ratio between upper layer and lower layer
after phase separation in culture medium

| Final concentration (w/v %) | | Upper layer (μL) | Lower layer (μL) |
|---|---|---|---|
| PEG | Dex | | |
| 5 | 5 | 170 | 130 |
| 6 | 4 | 220 | 80 |
| 7 | 3 | 260 | 40 |
| 8 | 2 | 280 | 20 |

The volume of the lower layer tended to decrease as the concentration of the polyether in the solution increased. From this tendency, it was considered that target molecules could be concentrated by selectively distributing them to the lower layer.

Example 1: Concentration of Extracellular Vesicles by Two-Phase Partition

Extracellular vesicles in blood serum were actually concentrated according to a polymer two-phase partition (PTPP) method established on the basis of the results of Experimental Example 1.

1. Method
1-1. Concentration of Extracellular Vesicles

Extracellular vesicles in a patient blood serum were concentrated according to the following procedure.

(1) A 30 w/v % aqueous PEG solution containing PEG6000, a 30 w/v % aqueous PEG solution containing PEG35000, and a 30 w/v % aqueous solution of Dex having a molecular weight of 500000 were prepared.

(2) Then, 200 μL of blood serum derived from a colon cancer patient and 200 μL of diluted blood serum obtained by diluting the blood serum with PBS 4-fold were added to different 1.5 mL-tubes, respectively.

(3) Then, 80 μL of the aqueous PEG solution containing PEG6000 or 80 μL of the aqueous PEG solution containing PEG35000 prepared in the above (1) was added to each of the blood serum-containing tubes and the diluted blood serum-containing tubes prepared in the above (2).

(4) Then, 20 μL of the aqueous Dex solution prepared in the above (1) was added to each of the tubes prepared in the above (3), and the mixture in each of the tubes was stirred several times by pipetting.

(5) The tubes were centrifuged with a tabletop microcentrifuge at 1,260 to 2,840 g for 1 minute.

(6) The liquid phase in each of the tubes was confirmed to be separated into upper and lower layers. The tubes were stored on ice.

1-2. ELISA Analysis of Extracellular Vesicles
1-2-1. Samples for ELISA Analysis

Samples for ELISA analysis were prepared according to the following procedure.

(1) First, 200 μL of the upper layer was collected from each of the tubes centrifuged in the above 1-1. (hereinafter referred to as "upper layer sample").

(2) Then, 50 μL of PBS was added to each of the tubes, from which the upper layer had been collected, to disperse a precipitate (hereinafter referred to as "lower layer sample").

(3) Each of the samples was stored at 4° C. until analysis.

1-2-2. Preparation of ELISA Analysis Plate

A 96-well plate for ELISA analysis was prepared according to the following procedure.

(1) Anti-CD9 antibody (BioLegend (USA)) as a capture antibody was diluted to 5 μg/mL, and 90 μL of the diluted antibody was added to each well of a 96-well plate (Immuno Plate (Thermo Fisher Scientific)), and the plate was allowed to stand at 4° C. overnight.

(2) Each well was washed three times with 250 μL of 0.05% Tween 20-added PBS (PBST), and the PBST was finally removed as much as possible.

1-2-3. ELISA Analysis

CD9 protein contained in extracellular vesicles was measured by ELISA according to the following procedure.

(1) In order to block the 96-well plate prepared in 1-2-2, 200 μL of PBST containing 1% BSA was added to each well, and the plate was allowed to stand at room temperature for 1 hour and 30 minutes.

(2) Each well was washed three times with 250 μL of PBST, and the PBST was finally removed as much as possible.

(3) Then, 50 μL of exosomes (derived from HCT116 cells) as a control, 50 μL of the upper layer sample prepared in the above 1-2-1, or 50 μL of the lower layer sample prepared in the above 1-2-1 was added to each well of the blocked 96-well plate.

(4) The 96-well plate was incubated at 37° C. for 2 hours while shaken at 400 rpm.

(5) After the completion of the reaction in the above (4), each well was washed three times with 250 μL of PBST, and the PBST was finally removed as much as possible.

(6) Alkaline phosphatase-labeled anti-CD9 antibody for detection was diluted 1,200-fold, and 50 μL of the diluted antibody was added to each well. The alkaline phosphatase-labeled anti-CD9 antibody was prepared using Alkaline Phosphase Labeling Kit (DOJINDO LABORATORIES, JAPAN) by labeling anti-CD9 antibody (BioLegend) with alkaline phosphatase according to a protocol attached to the kit.

(7) After the antibody for detection was added, the 96-well plate was incubated at 37° C. for 1 hour and 30 minutes while shaken at 400 rpm.

Figure 2:
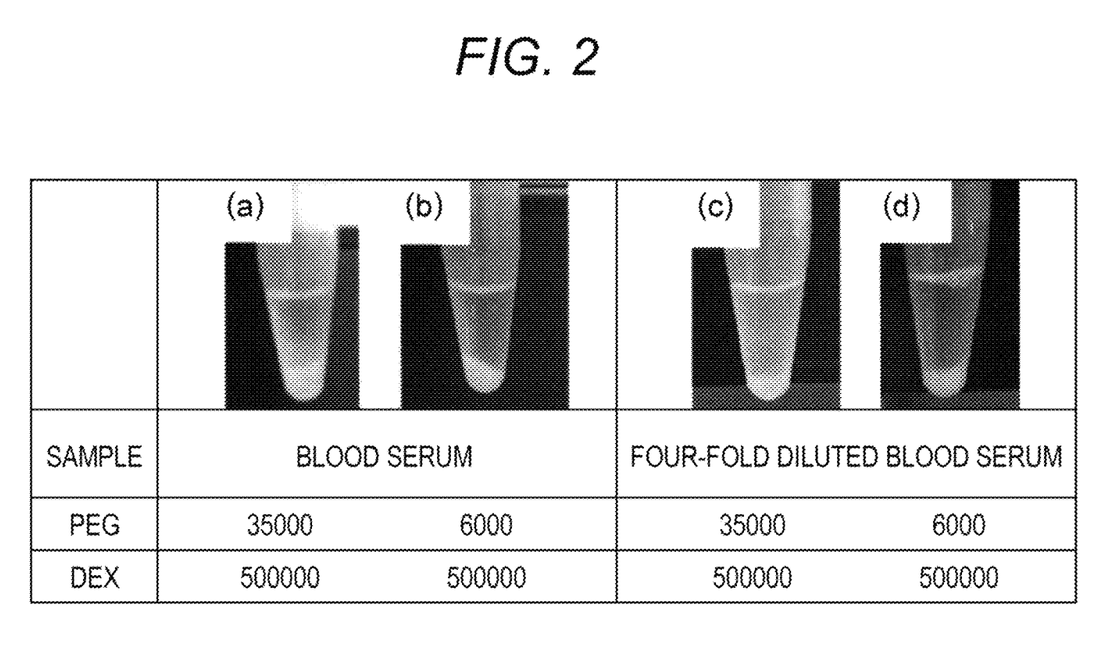
FIG. 2 shows photographs showing the results of concentration performed by a PEG6000-PTPP method and a PEG35000-PTPP method using blood serum and diluted blood serum as liquid samples.

(8) After the completion of the reaction in the above (7), each well was washed three times with 250 μL of PBST, and the PBST was finally removed as much as possible.
(9) HISCL luminescent substrates R4 and R5 (SYSMEX CORPORATION) were mixed at R4:R5=1:2, 100 μL of the thus obtained mixture was added to each well, and the 96-well plate was allowed to stand at room temperature for 10 minutes.
(10) Then, luminescence intensity was measured with a luminometer (Tecan Japan Co., Ltd.).
1-3. Results FIG. 2 shows the results of the PTPP method using PEG6000 (PEG6000-PTPP method) and the PTPP method using PEG35000 (PEG35000-PTPP method) performed on the blood serum and the diluted blood serum.

The upper layer corresponding to a second fraction obtained by the PEG35000-PTPP method was more remarkably whitish than that obtained by the PEG6000-PTPP method. From this, it was considered that in the case of the PEG35000-PTPP method, extracellular vesicles that had not been distributed to the lower layer were present in the upper layer without being concentrated. Further, it was considered that there was a fear that this reduced the concentration rate or collection rate of extracellular vesicles.

Figure 3:
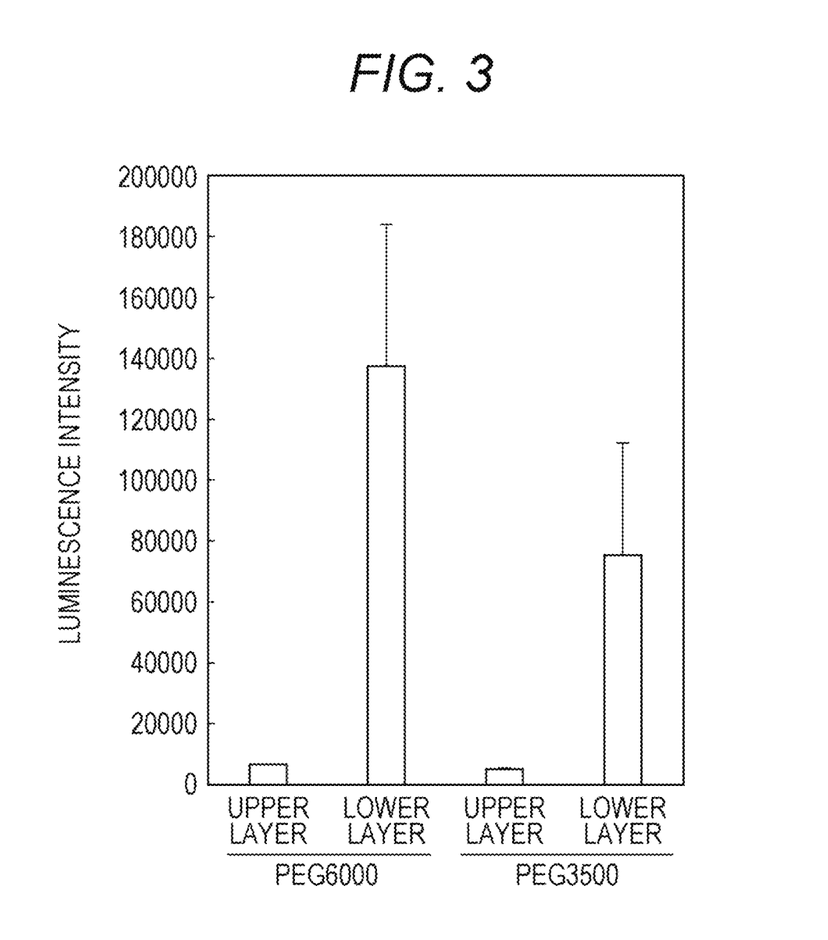
FIG. 3 shows the results of detection of CD9 contained in extracellular vesicles concentrated by the PTPP methods by ELISA methods.

Next, CD9 protein in extracellular vesicles was measured by ELISA, and the collection rate of extracellular vesicles was evaluated on the basis of the luminescence intensity of CD9 protein. FIG. 3 shows the luminescence intensities of the upper layer samples and the lower layer samples collected by performing the PEG6000-PTPP method and the PEG35000-PTPP method on the blood serum. In both cases where PEG6000 was used and where PEG35000 was used, almost all extracellular vesicles were contained in the lower layer. However, luminescence derived from CD9 protein in the lower layer sample collected by the PEG6000-PTPP method was stronger than that obtained by the PTPP method using PEG35000. From this, it was considered that the lower layer sample collected by the PEG6000-PTPP method contained a larger amount of extracellular vesicles.

Table 7 shows the collection rate of extracellular vesicles when the diluted blood serum was used.

PEG6000-PTPP method was 193.6, and that in the case of the PEG35000-PTPP method was 108.0. Further, the collection rate of extracellular vesicles was calculated from the total luminescence intensity of the lower layer sample and the upper layer sample obtained by the PTPP method and the luminescence intensity of the lower layer sample. As a result, the extracellular vesicle collection rate of the PEG6000-PTPP method was 45.5%, whereas the extracellular vesicle collection rate of the PEG35000-PTPP method was 27.2%, that is, the collection rate of the PEG6000-PTPP method was 1.7 times higher than that of the PEG35000-PTPP method.

This revealed that extracellular vesicles can be more efficiently concentrated using a polyether having a molecular weight lower than that of PEG35000 having a high molecular weight and used for concentrating extracellular vesicles in Balaj, N et al., Scientific Reports, 5, Article number: 13103 (2015) and Kim, J et al., PLoS ONE, DOI:10.1371/journal.pone.0129760 Jun. 19, 2015.

Example 2: Comparison Between Polymeric Precipitation Method and PTPP Method

1. Method

The collection rate of extracellular vesicles and operability were compared between the PTPP method according to the present invention and the polymeric precipitation method as a conventional method for concentrating extracellular vesicles.

As a sample used to concentrate extracellular vesicles, PBS containing exosomes (derived from HCT116 cells) as a control was used.

The PTPP method was performed using PEG6000 in the same manner as in 1-1 in Example 1.

Concentration of extracellular vesicles by the polymeric precipitation method was performed using EXO-Prep One step Exosome isolation Reagent (HansaBioMed) according to a protocol attached to the reagent (hereinafter referred to as "EXO-Prep method").

The collection rates of the above two methods were evaluated on the basis of the number of copies of miRNA21 (hereinafter also referred to as "miR21").

TABLE 7

Comparison between PEG6000-PTPP method and PEG35000-PTPP method

| | PBS | Four-fold diluted blood serum | | | |
|---|---|---|---|---|---|
| Sample | Lower layer (n) (Luminescence intensity) | Upper layer (Luminescence intensity) | Lower layer (s) (Luminescence intensity) | Lower layer/Upper layer | s/n ratio |
| PEG6000 | 711.3 | 6826.7 | 137734.3 | 20.2 | 193.6 |
| PEG35000 | 700.3 | 5266.3 | 75651.3 | 14.4 | 108.0 |

As shown in Table 7, the ratio between extracellular vesicles contained in the lower layer sample and extracellular vesicles contained in the upper layer sample (lower layer/upper layer) in the case of the PEG6000-PTPP method was 20.2 and that in the case of the PEG35000-PTPP method was 14.4. Further, when the luminescence intensity of a lower layer sample separated by performing the PEG6000-PTPP method or the PEG35000-PTPP method on PBS instead of the diluted blood serum was defined as n, and the luminescence intensity of the lower layer sample separated by performing the PEG6000-PTPP method or the PEG35000-PTPP method on the diluted blood serum was defined as s, the ratio of s to n (s/n ratio) in the case of the Total RNA was collected from an extracellular vesicle concentrate obtained by each of the methods with the use of High Pure miRNA isolation kit (Roche Diagnostics). Quantitative RT-PCR was performed using 1 μL of total RNA, and the number of copies of miR21 was measured. The quantitative RT-PCR was performed using TaqMan (trademark) MicroRNA Reverse Transcription Kit, TaqMan (trademark) MicroRNA Assays, TaqMan (trademark) Universal Master Mix II, and Applied Biosystems (trademark) 7500 fast (Thermo Fisher Scientific) according to protocols attached thereto. As a positive control, exosome-containing PBS before concentration of extracellular vesicles was used.

2. Results

Figure 4:
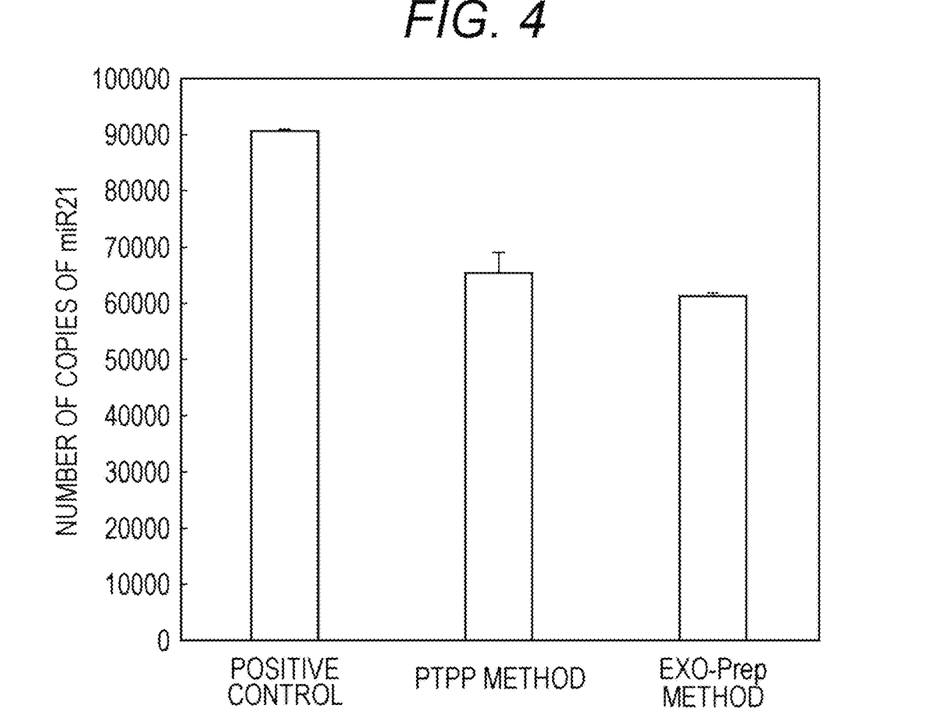
FIG. 4 is a graph showing the number of copies of miRNA21 contained in a positive control and the number of copies of miRNA21 contained in extracellular vesicles concentrated by the PTPP method or an EXO-Prep method.

FIG. 4 shows the number of copies of miR21 contained in the positive control, that contained in extracellular vesicles concentrated by the PTPP method, and that contained in extracellular vesicles concentrated by the EXO-Prep method. The number of copies of miR21 contained in the positive control represents the total number of copies of miR21 contained in 200 µL of the positive control. The collection rate of the PTPP method and that of the EXO-Prep method were determined on the basis of the total number of copies of miR21 of the positive control, and were found to be 72.1% and 67.5%, respectively. That is, the collection rate of the PTPP method was higher than that of the EXO-Prep method.

On the other hand, operability was compared between the PTPP method and the EXO-Prep method. As a result, the EXO-Prep method required about 1 hour to concentrate extracellular vesicles, but the PTPP method completed concentration in about 1 minute.

When the exosome fraction is used for measurement such as ELISA, it is necessary to disperse exosomes in a solution of some kind. The dispersibility of the concentrated exosome fraction was compared, and as a result, the exosome fraction obtained by the EXO-Prep method was present as a hard pellet at the bottom of the container, and therefore exosomes could not be completely dispersed even by pipetting for about 15 minutes. On the other hand, the exosome fraction obtained by centrifugation according to the present invention was also present as a pellet at the bottom of the container, but the pellet was soft and therefore exosomes could be dispersed in the solution by pipetting several times. Therefore, the time required for pipetting was about several seconds.

From the results, it was considered that the PTPP method was remarkably superior to the EXO-Prep method in the collection rate of extracellular vesicles, the time required to concentrate extracellular vesicles, and the operability of concentrated extracellular vesicles.

Example 3: Examination of Operability

The operability at the time of concentrating extracellular vesicles was compared between when PEG having a high molecular weight such as PEG35000 was used and when PEG having a relatively low molecular weight such as PEG6000 was used.

The ease of aspiration was compared between a 30 w/v % aqueous PEG6000 solution and a 30 w/v % aqueous PEG35000 solution using, as an indicator, the time required to aspirate 200 µL of each of the solutions with a Pipetman.

Figure 5:
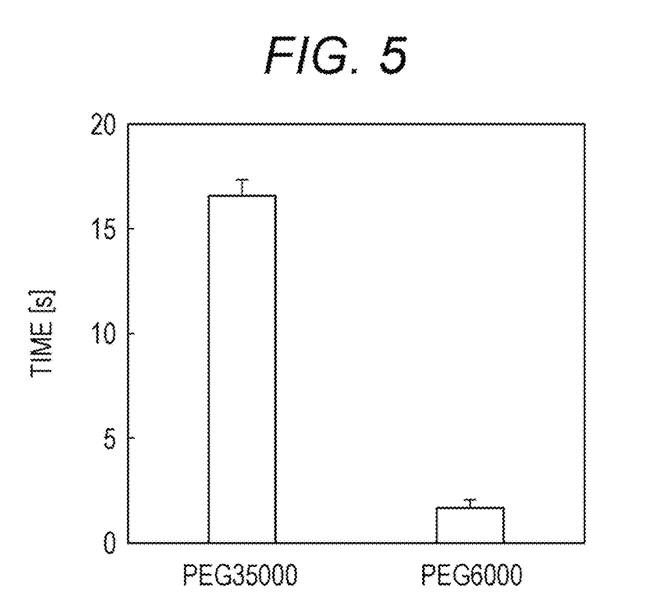
FIG. 5 is a graph showing the time taken to aspirate 200 μL of an aqueous PEG6000 solution or 200 μL of an aqueous PEG35000 solution with a Pipetman.

As shown in FIG. 5, it took 16 seconds or more to aspirate 200 µL of the aqueous PEG 35000 solution. On the other hand, the time required to aspirate the same amount of the aqueous PEG6000 solution was one-tenth or less that required to aspirate the aqueous PEG35000 solution. When the aspiration time is longer, there is a fear that pipetting or the speed of measuring time is different with each person or the amount of a reagent aspirated is different among independent experiments. Therefore, from the result, it was considered that when the aspiration time was longer, there was a possibility that the reproducibility of experiments could not be achieved. Further, it was considered that it was impractical to wait 16 seconds until the end of the aspiration of a reagent with a Pipetman.

For this reason, it was considered that from the viewpoint of high reproducibility of experiments and automatization of this technique, PEG6000 was more suitable because PEG6000 could be handled in a shorter time and a higher concentration rate could be achieved.

Further, it was revealed that when PEG35000 is used in high concentration, the viscosity of the mixture of PEG, Dex, and a sample increases, which deteriorates operability even at room temperature. In order to achieve excellent operability when PEG35000 is used, it was necessary to reduce the amount of high-molecular weight PEG, such as PEG35000, contained in the mixture of PEG, Dex, and a sample. In this case, however, phase separation did not occur unless the PTPP method was performed at 4° C. For this reason, it was considered that it was necessary to use PEG having a molecular weight lower than that of PEG35000 to perform the PTPP method with excellent operability at room temperature.

What is claimed is:

1. A method for concentrating extracellular vesicles, comprising:
   preparing a mixture comprising a first fraction and a second fraction, wherein said mixture is prepared by mixing a liquid sample comprising extracellular vesicles with a dextran having a weight average molecular weight of between 100,000 and 700,000, and with a polyethylene glycol having a number average molecular weight of between 8,980 and 18,400,
   wherein the first fraction comprises a higher concentration of extracellular vesicles than the second fraction, and the first fraction comprises a higher concentration of extracellular vesicles than the liquid sample,
   and wherein the liquid sample is blood serum, blood plasma, lymph fluid, urine, ascites, pleural effusion, cerebrospinal fluid, or interstitial fluid.

2. The method according to claim 1, further comprising collecting the first fraction after the step of preparing.

3. The method according to claim 1, wherein said method further comprises a step of centrifuging the mixture after the mixing.

4. The method according to claim 3, wherein the centrifuging is performed at less than 10,000 g.

5. The method according to claim 3, wherein the centrifuging is performed for 2 minutes or less.

6. The method according to claim 3, wherein said mixing comprises stirring the mixture.

7. The method according to claim 3, wherein
   the first fraction is a fraction that comprises the dextran and is substantially free from the polyethylene glycol, and
   the second fraction is a fraction that comprises the polyethylene glycol and is substantially free from the dextran.

8. The method according to claim 1, wherein the mixture has a polyethylene glycol concentration of 4 w/v % or more.

9. The method according to claim 1, wherein the mixture has a dextran concentration of 2 w/v % or more.

10. The method according to claim 1, wherein said mixture is prepared by:
   mixing the liquid sample, a reagent comprising the dextran and a reagent comprising the polyethylene glycol; or
   mixing the liquid sample and a reagent comprising the dextran and the polyethylene glycol.

* * * * *